(12) United States Patent
Toida

(10) Patent No.: US 6,628,401 B2
(45) Date of Patent: Sep. 30, 2003

(54) OPTICAL TOMOGRAPHY IMAGING METHOD AND APPARATUS

(75) Inventor: Masahiro Toida, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/803,642

(22) Filed: Mar. 12, 2001

(65) Prior Publication Data

US 2001/0052982 A1 Dec. 20, 2001

(30) Foreign Application Priority Data

Mar. 10, 2000 (JP) ........................................ 2000-067264

(51) Int. Cl.$^7$ .............................. G01B 9/02; G02B 6/02
(52) U.S. Cl. ........................................ 356/479; 356/450
(58) Field of Search ................................ 356/479, 450, 356/497, 487, 345, 346, 349, 351, 357, 360; 600/425

(56) References Cited

U.S. PATENT DOCUMENTS

| | | | |
|---|---|---|---|
| 5,321,501 A | | 6/1994 | Swanson et al. |
| 5,555,087 A | | 9/1996 | Miyagawa et al. |
| 5,579,429 A | | 11/1996 | Naum |
| 6,002,480 A | * | 12/1999 | Izatt et al. ................. 356/345 |
| 6,006,128 A | | 12/1999 | Izatt et al. |
| 6,134,003 A | * | 10/2000 | Tearney et al. ............. 356/345 |
| 6,141,475 A | * | 10/2000 | Lawrence et al. .......... 385/123 |
| 6,198,540 B1 | * | 3/2001 | Ueda et al. ................. 356/349 |

FOREIGN PATENT DOCUMENTS

DE 199 04 565 A 9/1999
EP 0 785 600 A 7/1997

OTHER PUBLICATIONS

Optics Letters, vol. 21, No. 22, pp. 1839–1841, 1996.
Rao Y–J et al.: "Recent Progress in Fibre Optic Low–Coherence Interferometry" Measurement Science and Technology, IOP Publishing, Bristol, GB, vol. 7, No. 7, Jul. 1, 1996, pp. 981–999, XP000632360 ISSN: 0957–0233 * paragraphs '0001!,'05.7!, '05.8!; figures 13, 14 *.
Takada K et al: "High–Sensitivity Low Coherence Reflectometer Using Erbium–Doped Superfluorescent Fibre Source and Erbium–Doped Power Amplifier" Electronics Letters, IEE Stevenage, GB, vol. 29, No. 4, Feb. 18, 1993, pp. 365–367, XP000346066 ISSN: 0013–5194 * p. 365, right–hand column—p. 366, left–hand column *.
Hideur A et al: "Dynamics and stabilization of a high power side–pumped Yb–doped double–clad fiber laser" Optics Communications, North–Holland Publishing Co. Amsterdam, NL, vol. 186, No. 4–6, Dec. 15, 2000, pp. 311–317, XP004227060 ISSN: 0030–4018 * paragraph '0001!; figure 1 *.

* cited by examiner

Primary Examiner—Constantine Hannaher
Assistant Examiner—Otilia Gabor
(74) Attorney, Agent, or Firm—Sughrue Mion, PLLC

(57) ABSTRACT

Amplified spontaneous emission light, which is low coherence light radiated out from an optical fiber doped with a light emitting material when excitation energy is applied to the optical fiber, is divided into signal light and reference light. A frequency of the reference light is shifted to a frequency slightly different from the frequency of the signal light. A tomographic image of a measuring site is acquired from an intensity of interference light formed by the signal light reflected from the measuring site and the reference light.

17 Claims, 1 Drawing Sheet

OPTICAL TOMOGRAPHY IMAGING METHOD AND APPARATUS

BACKGROUND OF THE INVENTION

1. Field of the Invention

This invention relates to an optical tomography imaging method and apparatus, wherein a signal light beam, which is a low coherence light beam, is irradiated to a measuring site, and a tomographic image of the measuring site is thereby acquired. This invention particularly relates to an optical tomography imaging method and apparatus, wherein fine structure information at a surface of a measuring site and a deep portion of the measuring site is imaged in accordance with a reflected light beam of a signal light beam.

2. Description of the Related Art

Optical tomography imaging apparatuses utilizing a low coherence light beam, particularly optical tomography imaging apparatuses, in which an optical intensity of a low coherence interference light beam is measured with a heterodyne detection technique and a tomographic image of a measuring site is thereby obtained, have heretofore been utilized for acquiring optical tomography images of fine structures under the eyeground retina.

With the optical tomography imaging apparatuses, a tomographic information is acquired by dividing a low coherence light beam, which has been radiated out from a light source comprising a super luminescent diode (SLD), or the like, into a signal light beam and a reference light beam, slightly shifting a frequency of the reference light beam with a piezo-electric device, or the like, irradiating the signal light beam to a measuring site, causing reflected light beam of the signal light beam, which has been reflected from a predetermined depth in the measuring site, and the reference light beam to interfere with each other, and measuring the optical intensity of the interference light beam with the heterodyne detection technique. The information at the deep portion of the measuring site has heretofore been acquired by slightly moving a moving mirror, or the like, which is located in an optical path of the reference light beam, thereby altering an optical path length of the reference light beam, and causing the optical path length of the reference light beam and the optical path length of the signal light beam to coincide with each other.

In the optical tomography imaging apparatuses described above, in order for the tomographic information at the desired depth in the measuring site to be obtained, it is ideal that the interference of the signal light beam and the reference light beam with each other occurs only when the optical path length of the reference light beam and the optical path length of the signal light beam perfectly coincide with each other. However, actually, in cases where the difference between the optical path length of the signal light beam and the optical path length of the reference light beam is equal to at most a coherence length determined by the light source, the interference of the signal light beam and the reference light beam with each other occurs. Specifically, resolution in the low coherence interference is determined by the coherence length, which is determined by the light source.

In cases where a wavelength distribution of the light beam produced by the light source is a Gaussian distribution, a coherence length $\Delta L$ is represented by Formula (1) shown below.

$$\Delta L = (2/\pi) \cdot \ln 2 \cdot (\lambda c / \Delta \lambda) \quad (1)$$

wherein $\lambda c$ represents the center wavelength, and $\Delta \lambda$ represents the spectral width.

For example, in cases where a SLD producing a light beam having a center wavelength of 800 nm and a spectral width of 20 nm is employed as the light source, the coherence length becomes equal to approximately 14 $\mu$m. Therefore, in cases where the SLD having the characteristics described above is employed as the light source in the conventional optical tomography imaging apparatuses described above, the resolution becomes equal to approximately 14 $\mu$m. Accordingly, with the conventional optical tomography imaging apparatuses described above, in cases where the measuring site has a plurality of layers falling within a thickness approximately equal to the resolution, reflected light beams coming from the respective layers could not be discriminated from one another.

Recently, in the clinical fields, usefulness of tomographic images of living body tissues, and the like, has been known widely, and it is desired that, besides tomographic images of the eyeball site, tomographic images of living body tissues, which exhibit higher light scattering than the eyeball site, be acquired with a high resolution. For such purposes, it is necessary to utilize a light source, which is capable of producing a low coherence light beam having a high intensity and a short coherence length. However, with the SLD, the out put cannot always be enhanced. Also, with the SLD, the problems occur in that, since the spectral width is determined by a band gap, the spectral width cannot be set at a large value and the coherence length cannot be set to be short.

Therefore, an optical tomography imaging apparatus, in which a light source provided with a KLM mode-locked Ti:sapphire laser is utilized, has been proposed in, for example, "Optics Letters," Vol. 21, No. 22, pp. 1839 to 1841, by B. E. Bouma, et al., 1996. With the proposed optical tomography imaging apparatus, a low coherence light beam having a high intensity and a wide spectral width is obtained by the utilization of an ultrashort pulsed light beam and dispersion delay of an optical fiber and is utilized as a signal light beam and a reference light beam, such that a tomographic image is capable of being acquired with a high resolution.

However, the optical tomography imaging apparatus described above, in which the light source provided with the KLM mode-locked Ti:sapphire laser is utilized, has the problems in that the light source section is large in size, high in cost, and hard to process. Thus the optical tomography imaging apparatus described above, in which the light source provided with the KLM mode-locked Ti:sapphire laser is utilized, practically has the problems with regard to the size, the cost, and the processing of the apparatus.

SUMMARY OF THE INVENTION

The primary object of the present invention is to provide an optical tomography imaging method for acquiring a tomographic image by the utilization of low coherence interference, wherein a light source, which is large in size, high in cost, and hard to process, need not be utilized, and tomographic information is capable of being acquired with a high resolution.

Another object of the present invention is to provide an apparatus for carrying out the optical tomography imaging method.

The present invention provides an optical tomography imaging method, comprising the steps of:

i) dividing a low coherence light beam into a signal light beam and a reference light beam, ii) irradiating the signal light beam to a measuring site, iii) shifting a frequency of the reference light beam to a frequency having a slight frequency difference from the frequency of the signal light beam, iv) causing a reflected light beam of the signal light beam, which has been reflected from a predetermined deep portion of the measuring site, and the reference light beam to interfere with each other, an interference light beam being thereby obtained, v) measuring an intensity of the interference light beam, and vi) acquiring an optical tomography image of the measuring site in accordance with the measured intensity of the interference light beam, wherein the low coherence light beam is an amplified spontaneous emission light beam, which is radiated out from an optical fiber having been doped with a light emitting material when excitation energy is applied to the optical fiber.

The present invention also provides an optical tomography imaging apparatus, comprising:

i) means for dividing a low coherence light beam into a signal light beam and a reference light beam, ii) means for irradiating the signal light beam to a measuring site, iii) means for shifting a frequency of the reference light beam to a frequency having a slight frequency difference from the frequency of the signal light beam, iv) means for causing a reflected light beam of the signal light beam, which has been reflected from a predetermined deep portion of the measuring site, and the reference light beam to interfere with each other, an interference light beam being thereby obtained, v) means for measuring an intensity of the interference light beam, and vi) means for acquiring an optical tomography image of the measuring site in accordance with the measured intensity of the interference light beam, wherein the low coherence light beam is an amplified spontaneous emission light beam, which is radiated out from an optical fiber having been doped with a light emitting material when excitation energy is applied to the optical fiber.

The term "light emitting material" as used herein means a material having properties such that the material is capable of being excited by excitation energy applied from the exterior, and the excitation energy is thereby radiated out as light from the material. Also, the term "reflected light beam of a signal light beam having been reflected from a predetermined deep portion of a measuring site" as used herein means both the reflected light beam, which has been reflected from the predetermined deep portion of the measuring site, and the reflected light beam, which has been reflected from the surface of the measuring site.

The term "measuring an intensity of an interference light beam" as used herein means the measurement of the intensity of a beat signal (i.e., the interference light beam), the intensity of which repeatedly becomes high and low at a frequency equal to the difference between the frequencies of the signal light beam and the reference light beam. By way of example, the measurement may be made with a heterodyne interferometer.

In the optical tomography imaging method and apparatus in accordance with the present invention, the measuring site should preferably be a site of living body tissues, and a wavelength of the low coherence light beam should preferably fall within the range of 600 nm to 1700 nm.

Also, the excitation energy should preferably be energy of excitation light having a wavelength falling with in a wave length region of 500 nm to 1700 nm.

Further, the light emitting material should preferably be a dye capable of producing fluorescence.

Furthermore, the light emitting material may be selected from the group consisting of transition metal ions, rare earth element ions, and complex ions.

Also, the light emitting material may be at least one kind of ion selected from the group consisting of $Cr^{3+}$, $Mn^{4+}$, $Mn^{2+}$, $Fe^{3+}$, which are transition metal ions; $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, which are rare earth element ions; and $WO_4^{2-}$, $MoO_4^{2-}$, $VO_4^{3+}$, $Pt(CN)_4^{2-}$, and $WO_6^{6-}$, which are complex ions.

With the optical tomography imaging method and apparatus in accordance with the present invention, as the low coherence light beam for forming the signal light beam and the reference light beam, the amplified spontaneous emission light beam, which is radiated out from the optical fiber having been doped with the light emitting material when the excitation energy is applied to the optical fiber, is utilized. Therefore, the low coherence light beam having a high intensity and a wide spectral width is capable of being obtained from a light source, which is small in size, low in cost, and easy to process. Accordingly, the light source provided with an ultrashort pulse laser, or the like, which light source was necessary in the conventional optical tomography imaging apparatuses and is large in size, high in cost, and hard to process, need not be utilized, and the resolution in low coherence interference is capable of being enhanced.

Also, with the optical tomography imaging method and apparatus in accordance with the present invention, wherein the measuring site is a site of living body tissues, and the wavelength of the low coherence light beam falls within the range of 600 nm to 1700 nm, the signal light beam has desirable transmission characteristics and desirable scattering characteristics at the measuring site. Therefore, a desired tomographic image is capable of being acquired.

Further, with the optical tomography imaging method and apparatus in accordance with the present invention, wherein the excitation energy is energy of the excitation light having a wavelength falling within the wavelength region of 500 nm to 1700 nm, the light emitting material, which has been doped in the optical fiber, is capable of being excited efficiently.

Furthermore, with the optical tomography imaging method and apparatus in accordance with the present invention, wherein the light emitting material is the dye capable of producing the fluorescence, the low coherence light beam having a desirable center wavelength and a desired spectral width is capable of being obtained.

Also, with the optical tomography imaging method and apparatus in accordance with the present invention, wherein the light emitting material is selected from the group consisting of transition metal ions, rare earth element ions, and complex ions, the light emitting material is capable of being easily doped in the optical fiber. Further, the low coherence light beam having a desirable center wavelength and a desired spectral width is capable of being obtained.

Furthermore, with the optical tomography imaging method and apparatus in accordance with the present invention, the light emitting material may be at least one kind of ion selected from the group consisting of $Cr^{3+}$, $Mn^{4+}$, $Mn^{2+}$, $Fe^{3+}$, which are transition metal ions; $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, which are rare earth element ions; and $WO_4^{2-}$, $MoO_4^{2-}$, $VO_4^{3+}$, $Pt(CN)_4^{2-}$, and $WO_6^{6-}$, which are complex ions. In such cases, the excitation light is capable of being efficiently converted into the desired low coherence light beam.

DESCRIPTION OF THE PREFERRED EMBODIMENTS

Figure 1:
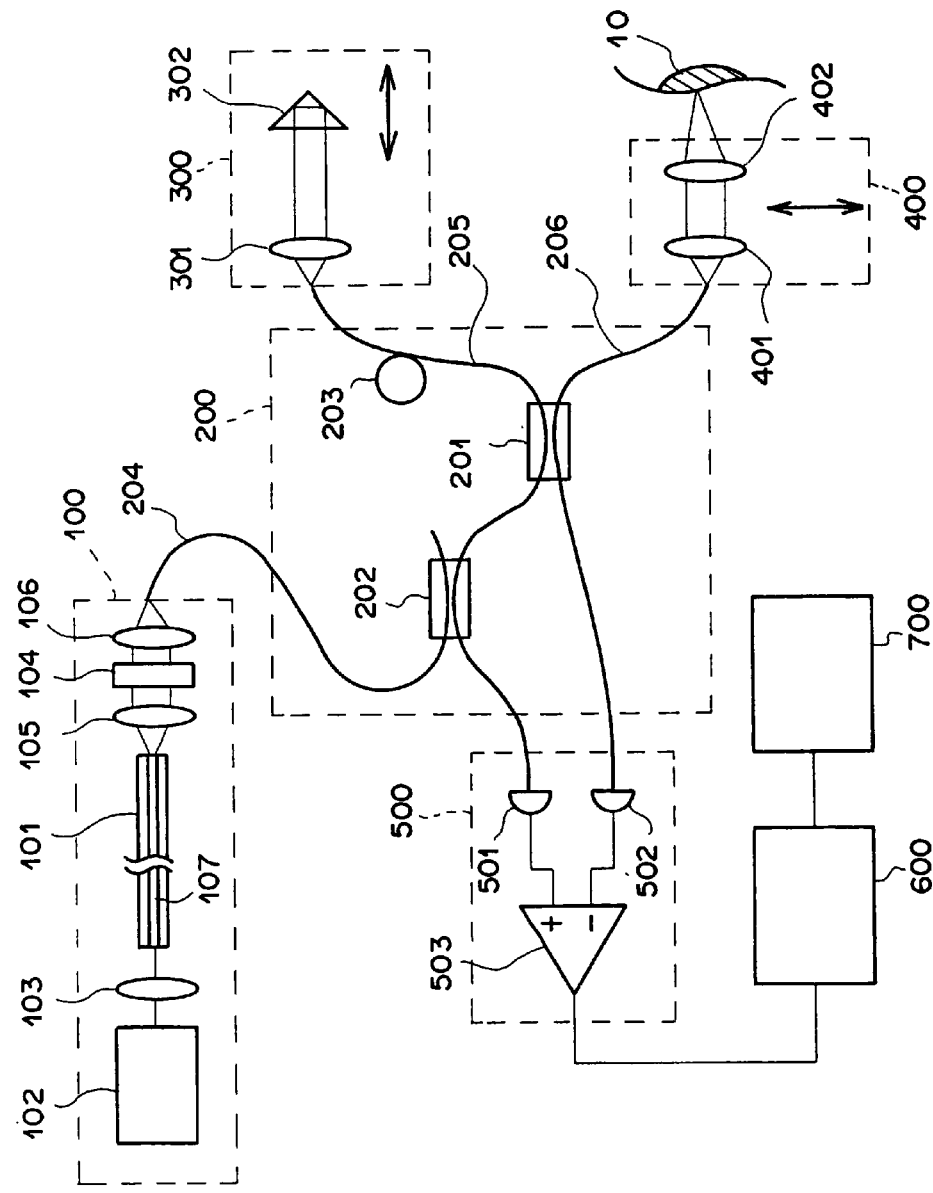
FIG. 1 is a schematic view showing an embodiment of the optical tomography imaging apparatus in accordance with the present invention.

The present invention will herein below be described in further detail with reference to the accompanying drawing.

FIG. 1 is a schematic view showing an embodiment of the optical tomography imaging apparatus in accordance with the present invention.

With reference to FIG. 1, the optical tomography imaging apparatus comprises a light source section 100 for radiating out a low coherence light beam having a center wavelength of 800 nm and a spectral width of approximately 200 nm. The optical tomography imaging apparatus also comprises a fiber coupling optical system 200 for dividing the low coherence light beam, which has been radiated out from the light source section 100, into a reference light beam Lr and a signal light beam Ls and combining the reference light beam Lr and a signal light beam Ls', which is a reflected light beam of the signal light beam Ls having been reflected from a predetermined plane (or a predetermined deep portion) in a measuring site 10 of living body tissues, with each other. The optical tomography imaging apparatus further comprises an optical path delay section 300, which is located in an optical path of the reference light beam Lr and alters an optical path length of the reference light beam Lr. The optical tomography imaging apparatus still further comprises a light scanning section 400 for scanning the measuring site 10 with the signal light beam Ls. The optical tomography imaging apparatus also comprises a balancing and difference detecting section 500 for detecting an intensity of an interference light beam Lc, which is formed from the interference of the signal light beam Ls', which is the reflected light beam of the signal light beam Ls having been reflected from the predetermined plane in the measuring site 10, and the reference light beam Lr with each other. The optical tomography imaging apparatus further comprises a signal processing section 600, which performs heterodyne detection for detecting the intensity of the signal light beam Ls' having been reflected from the predetermined plane in the measuring site 10. The intensity of the signal light beam Ls' is detected from the optical intensity of the interference light beam Lc having been detected by the balancing and difference detecting section 500. The signal processing section 600 also converts the detected intensity of the signal light beam Ls' into an image signal. The optical tomography imaging apparatus still further comprises an image displaying section 700 for reproducing a tomographic image from the image signal, which has been obtained from the signal processing section 600, and displaying the tomographic image.

The light source section 100 comprises a fiber light source 101, which produces the low coherence light beam when excitation light is irradiated to the fiber light source 101. The light source section 100 also comprises a semiconductor laser 102 for producing a laser beam having a wavelength of 660 nm, which laser beam acts as the excitation light for exciting the fiber light source 101. The light source section 100 further comprises a lens 103 for converging the excitation light onto an entry end face of the fiber light source 101. The light source section 100 still further comprises an excitation light cut-off filter 104 for filtering out light having wavelengths falling within a wavelength region of at most 700 nm, such that the excitation light mixed in the low coherence light beam may be filtered out. The light source section 100 also comprises a lens 105 and a lens 106 for converging the low coherence light beam, which has been produced by the fiber light source 101.

The fiber light source 101 is constituted of an optical fiber having a core 107, which extends along the center line of the optical fiber. The core 107 has been doped with a dye, which is capable of absorbing the excitation light and emitting light. When the excitation light impinges upon the entry end face of the fiber light source 101, the low coherence light beam having the center wavelength of approximately 800 nm and the spectral width of approximately 200 nm is radiated out from a radiating end face of the fiber light source 101.

The fiber coupling optical system 200 comprises a fiber coupler 201 for dividing the low coherence light beam, which has been produced by the fiber light source 101 and has been radiated out from the light source section 100, into the reference light beam Lr and the signal light beam Ls and combining the reference light beam Lr and the signal light beam Ls', which is the reflected light beam of the signal light beam Ls having been reflected from the predetermined deep portion of the measuring site 10, with each other in order to obtain the interference light beam Lc. The fiber coupling optical system 200 also comprises a fiber coupler 202, which is located between the light source section 100 and the fiber coupler 201. The fiber coupling optical system 200 further comprises a piezo-electric device 203 for slightly shifting the frequency of the reference light beam Lr. The fiber coupling optical system 200 still further comprises a fiber 204 for connecting the light source section 100 and the fiber coupler 202 with each other. The fiber coupling optical system 200 also comprises a fiber 205 for connecting the optical path delay section 300 and the balancing and difference detecting section 500 via the fiber couplers 201 and 202. The fiber coupling optical system 200 further comprises a fiber 206 for connecting the light scanning section 400 and the balancing and difference detecting section 500 with each other via the fiber coupler 201. The fibers 204, 205, and 206 are single mode optical fibers.

The optical path delay section 300 comprises a lens 301 for collimating the reference light beam Lr, which has been radiated out from the fiber 205, and causing the reflected reference light beam Lr to impinge upon the fiber 205. The optical path delay section 300 also comprises a prism 302, which is moved in the horizontal direction in FIG. 1 and thereby alters the optical path length of the reference light beam Lr.

The light scanning section 400 comprises a lens 401 and a lens 402, which alter the position of the signal light beam Ls in the vertical direction in FIG. 1. The lens 401 and the lens 402 also cause the signal light beam Ls', which has been reflected from the measuring site 10, to impinge upon the fiber 206.

The balancing and difference detecting section 500 comprises a photodetector 501 and a photodetector 502 for measuring the optical intensity of the interference light beam Lc. The balancing and difference detecting section 500 also comprises a differential amplifier 503 for adjusting the input balance of the value having been detected by the photodetector 501 and the value having been detected by the photodetector 502, canceling noise components and drift components, and amplifying the difference.

How the embodiment of the optical tomography imaging apparatus operates will be described hereinbelow.

Firstly, the excitation light having the wavelength of 660 nm is produced by the semiconductor laser 102, converged by the lens 103, and introduced into the core 107 of the fiber light source 101.

The excitation light propagates through the core 107 and is absorbed by the dye having been doped in the core 107. The dye having absorbed the excitation light transits from a ground state to an excited state. The dye returns from the excited state to the ground state via thermal relaxation and light emission processes. Since the fiber light source 101 does not constitute an optical resonator, respective light components emitted by the dye are amplified randomly without any correlation, propagated through the core 107, and radiated out as a spontaneous emission light beam from the radiating end face of the fiber light source 101. The spontaneous emission light beam is the low coherence light beam having spectral characteristics, which are determined by an emission spectrum of the dye having been doped in the core 107 and transmission characteristics of the fiber light source 101. Also, the optical intensity of the spontaneous emission light beam depends upon the optical intensity of the excitation light and the amount of the dye having been doped in the core 107. Specifically, the low coherence light beam having the desired center wavelength, the desired spectral width, and the desired optical intensity is capable of being obtained by appropriately selecting the optical intensity of the excitation light, the kind and the amount of the dye doped in the core 107 of the fiber light source 101, and the length of the fiber light source 101.

In this embodiment, the low coherence light beam having the center wavelength of approximately 800 nm and the spectral width of approximately 200 nm is radiated out from the fiber light source 101. The low coherence light beam is collimated by the lens 105 and passes through the excitation light cut-off filter 104. Thereafter, the low coherence light beam is converged by the lens 106 and introduced into the fiber 204.

The low coherence light beam, which has passed through the fiber 204, is introduced by the fiber coupler 202 into the fiber 205. Also, the low coherence light beam is dived by the fiber coupler 201 into the reference light beam Lr, which travels through the fiber 205 toward the optical path delay section 300, and the signal light beam Ls, which travels through the fiber 206 toward the light scanning section 400.

The reference light beam Lr is modulated by the piezo-electric device 203, which is located in the optical path of the reference light beam Lr, and a slight frequency difference Δf occurs between the reference light beam Lr and the signal light beam Ls.

The signal light beam Ls passes through the lens 401 and the lens 402 of the light scanning section 400 and impinges upon the measuring site 10. The signal light beam Ls' of the signal light beam Ls impinging upon the measuring site 10, which signal light beam has been reflected from the predetermined depth in the measuring site 10, returns through the lens 402 and the lens 401 into the fiber 206. At the fiber coupler 201, the signal light beam Ls', which has returned into the fiber 206, is combined with the reference light beam Lr, which has returned into the fiber 205 in the manner described later.

The reference light beam Lr, which has been modulated by the piezo-electric device 203, passes through the fiber 205 and then passes through the lens 301 of the optical path delay section 300. The reference light beam Lr having passed through the lens 301 impinges upon the prism 302 and is reflected by the prism 302. The reference light beam Lr having been reflected by the prism 302 again passes through the lens 301 and returns into the fiber 205. At the fiber coupler 201, the reference light beam Lr having returned into the fiber 205 is combined with the signal light beam Ls' described above.

The signal light beam Ls' and the reference light beam Lr, which have been combined with each other by the fiber coupler 201, are coaxially superposed one upon the other. When predetermined conditions are satisfied, the signal light beam Ls' and the reference light beam Lr interfere with each other. As a result, the interference light beam Lc is formed, and the beat signal occurs.

Each of the reference light beam Lr and the signal light beam Ls' is the low coherence light beam having a short coherence length. Therefore, in cases where the optical path length of the signal light beam Ls (Ls') traveling from the position, at which the low coherence light beam is divided into the signal light beam Ls and the reference light beam Lr, to the position of the fiber coupler 201, to which the signal light beam Ls' returns, is approximately equal to the optical path length of the reference light beam Lr traveling from the position, at which the low coherence light beam is divided into the signal light beam Ls and the reference light beam Lr, to the position of the fiber coupler 201, to which the reference light beam Lr returns, the signal light beam Ls' and the reference light beam Lr interfere with each other. As a result, the beat signal, the intensity of which repeatedly becomes high and low at the frequency equal to the difference (Δf) between the frequencies of the signal light beam Ls' and the reference light beam Lr interfering with each other, occurs.

The interference light beam Lc is divided by the fiber coupler 201 into two interference light beams Lc, Lc. One of the divided interference light beams Lc, Lc passes through the fiber 205 and impinges upon the photodetector 501 of the balancing and difference detecting section 500. The other interference light beam Lc passes through the fiber 206 and impinges upon the photodetector 502 of the balancing and difference detecting section 500.

The photodetector 501 and the photodetector 502 detect the optical intensity of the beat signal from the interference light beam Lc. Also, the differential amplifier 503 calculates the difference between the value detected by the photodetector 501 and the value detected by the photodetector 502. The differential amplifier 503 feeds out the information representing the calculated difference into the signal processing section 600. The differential amplifier 503 is provided with the functions for adjusting the balance of direct current components of the input values. Therefore, in cases where drift occurs in the low coherence light beam having been radiated out fro the light source section 100, the balance of the direct current components is capable of being adjusted and the difference is capable of being amplified. In this manner, the drift components are canceled, and only the beat signal components are detected.

In such cases, when the prism 302 is moved in the optical axis direction (i.e., horizontally in FIG. 1), the optical path length of the reference light beam Lr traveling from the position, at which the low coherence light beam is divided into the signal light beam Ls and the reference light beam Lr, to the position of the fiber coupler 201, to which the reference light beam Lr returns, alters. As a result, the optical path length of the signal light beam Ls (Ls'), which is capable of undergoing the interference with the reference light beam Lr, also alters. Therefore, the tomographic information at a different depth in the measuring site 10 is capable of being acquired.

With the operations described above, the tomographic information at planes, which range from the surface and the desired deep portion, at the predetermined point of the measuring site 10 is acquired. Thereafter, with the lens 401 and the lens 402 of the light scanning section 400, the incidence point of the signal light beam Ls upon the measuring site 10 is slightly shifted vertically in FIG. 1. Also, in the same manner as that described above, the tomographic information at planes, which range from the surface and the predetermined deep portion, at the new point of the measuring site 10 is acquired. The operations described above are iterated, and tomographic images of the measuring site 10 are capable of being acquired.

The signal processing section 600 performs the heterodyne detection for detecting the intensity of the signal light beam Ls', which has been reflected from the predetermined plane in the measuring site 10, in accordance with the optical intensity of the interference light beam Lc, which optical intensity has been detected by the balancing and difference detecting section 500. The detected intensity of the signal light beam Ls' is converted into an image signal. Also, a tomographic image is reproduced from the image signal and displayed at the image displaying section 700.

The center wavelength of the low coherence light beam radiated out from the light source section 100 is 800 nm, and the spectral width of the low coherence light beam is 200 nm. Therefore, with Formula (1) shown above, the coherence length is calculated to be 1.4 μm. Specifically, the resolution in the low coherence interference becomes equal to 1.4 μm.

Accordingly, the light source provided with an ultrashort pulse laser, or the like, which light source was necessary in the conventional optical tomography imaging apparatuses and is large in size, high in cost, and hard to process, need not be utilized, and the resolution in the low coherence interference is capable of being enhanced to a high resolution, with which the fine tomographic image of the living body tissues, or the like, is capable of being acquired.

Also, the wavelength of the low coherence light beam falls within the range of approximately 700 nm to approximately 900 nm. Therefore, the signal light beam Ls has desirable transmission characteristics and desirable scattering characteristics at the measuring site 10 of the living body tissues. Therefore, a desired tomographic image is capable of being acquired.

Further, the excitation energy is energy of the laser beam having the wavelength of 660 nm, which laser beam is produced by the semiconductor laser 102. Therefore, the dye, which has been doped in the fiber light source 101, is capable of being excited efficiently.

In this embodiment, the fiber light source 101 is capable of being changed over to a different one. Therefore, in accordance with the light transmission characteristics and the light scattering characteristics of the measuring site 10, the center wavelength and the spectral width of the low coherence light beam are capable of being selected appropriately. Accordingly, usefulness of the optical tomography imaging apparatus is capable of being enhanced even further.

In the embodiment described above, the semiconductor laser 102 is employed as the excitation light source. Alternatively, in lieu of the semiconductor laser 102, a YAG laser for producing a second harmonic having a wavelength of 660 nm may be employed. In such cases, the excitation light having an enhanced intensity is capable of being obtained. Therefore, the low coherence light beam having an enhanced intensity is capable of being obtained.

In a modification of the embodiment described above, in lieu of the fiber light source 101 having been doped with the dye, a fiber light source having been doped with a light emitting material selected from the group consisting of transition metal ions, rare earth element ions, and complex ions, may be employed. The above-enumerated ions are capable of being easily doped in the core of the fiber light source. Therefore, in cases where the above-enumerated ions are utilized, the production cost of the fiber light source is capable of being kept low. Also, as the light emitting material, it is possible to employ at least one kind of ion selected from the group consisting of $Cr^{3+}$, $Mn^{4+}$, $Mn^{2+}$, $Fe^{3+}$, which are transition metal ions; $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, which are rare earth element ions; and $WO_4^{2-}$, $MoO_4^{2-}$, $VO_4^{3+}$, $Pt(CN)_4^{2-}$, and $WO_6^{6-}$, which are complex ions. In such cases, the excitation light is capable of being efficiently converted into the low coherence light beam having the desired center wavelength and the desired spectral width.

What is claimed is:

1. An optical tomography imaging method, comprising:
    i) dividing a low coherence light beam into a signal light beam and a reference light beam,
    ii) irradiating the signal light beam to a measuring site,
    iii) shifting a frequency of the reference light beam to a frequency having a slight frequency difference from the frequency of the signal light beam,
    iv) causing a reflected light beam of the signal light beam, which has been reflected from a predetermined deep portion of the measuring site, and the shifted reference light beam to interfere with each other, a heterodyne interference light beam being thereby obtained,
    v) dividing the heterodyne interference light beam into first and second divided interference light beams,
    vi) measuring an intensity of the first and second divided interference light beams, and
    vii) acquiring an optical tomography image of the measuring site in accordance with the measured intensity of the first and second divided interference light beams,
    wherein the low coherence light beam is an amplified spontaneous emission light beam, which is radiated out from an optical fiber having been doped with a light emitting material, when excitation energy is applied to the optical fiber.

2. A method as defined in claim 1 wherein the measuring site is a site of living body tissues, and
    a wavelength of the low coherence light beam falls within the range of 600 nm to 1700 nm.

3. A method as defined in claim 2 where in the excitation energy is energy of excitation light having a wavelength falling within a wavelength region of 500 nm to 1700 nm.

4. A method as defined in claim 1, 2, or 3 wherein the light emitting material is a dye capable of producing fluorescence.

5. A method as defined in claim 1, 2, or 3 wherein the light emitting material is selected from the group consisting of transition metal ions, rare earth element ions, and complex ions.

6. A method as defined in claim 1, 2, or 3 wherein the light emitting material is at least one kind of ion selected from the group consisting of $Cr^{3+}$, $Mn^{4+}$, $Mn^{2+}$, $Fe^{3+}$, which are transition metal ions; $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, which are rare earth element ions; and $WO_4^{2-}$, $MoO_4^{2-}$, $VO_4^{3+}$, $Pt(CN)_4^{2-}$, and $WO_6^{6-}$, which are complex ions.

7. The method of claim 1 further comprising: guiding said signal light beam, reference light beam and heterodyne and first and second divided interference light beams over a physical medium.

8. The method of claim 7, wherein the signal light beam, reference light beam and heterodyne and first and second divided interference light beams are propagated in a single mode over the physical medium.

9. An optical tomography imaging apparatus, comprising:
  i) means for dividing a low coherence light beam into a signal light beam and a reference light beam,
  ii) means for irradiating the signal light beam to a measuring site,
  iii) means for shifting a frequency of the reference light beam to a frequency having a slight frequency difference from the frequency of the signal light beam,
  iv) means for causing a reflected light beam of the signal light beam, which has been reflected from a predetermined deep portion of the measuring site, and the shifted reference light beam to interfere with each other, a heterodyne interference light beam being thereby obtained,
  v) means for dividing the heterodyne interference light beam into first and second divided interference light beams and measuring an intensity of the first and second divided interference light beams, and
  vi) means for acquiring an optical tomography image of the measuring site in accordance with the measured intensity of the first and second divided interference light beams
  wherein the low coherence light beam is an amplified spontaneous emission light beam, which is radiated out from an optical fiber having been doped with a light emitting material, when excitation energy is applied to the optical fiber.

10. An apparatus as defined in claim 9 wherein the measuring site is a site of living body tissues, and
  a wavelength of the low coherence light beam falls within the range of 600 nm to 1700 nm.

11. An apparatus as defined in claim 10 wherein the excitation energy is energy of excitation light having a wavelength falling within a wavelength region of 500 nm to 1700 nm.

12. An apparatus as defined in claim 9, 10, or 11 wherein the light emitting material is a dye capable of producing fluorescence.

13. An apparatus as defined in claim 9, 10, or 11 wherein the light emitting material is selected from the group consisting of transition metal ions, rare earth element ions, and complex ions.

14. An apparatus as defined in claim 9, 10, or 11 wherein the light emitting material is at least one kind of ion selected from the group consisting of $Cr^{3+}$, $Mn^{4+}$, $Mn^{2+}$, $Fe^{3+}$, which are transition metal ions; $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, which are rare earth element ions; and $WO_4^{2-}$, $MoO_4^{2-}$, $VO_4^{3+}$, $Pt(CN)_4^{2-}$, and $WO_6^{6-}$, which are complex ions.

15. The apparatus of claim 9 further comprising: physical propagating medium interconnecting the means for irradiating the signal to the measuring site and the means for causing the reflected light beam and the reference light beam to interfere with each other.

16. The apparatus of claim 15, wherein the physical propagating medium propagates signal in a single mode.

17. An optical tomography imaging apparatus, comprising:
  i) means for dividing a low coherence light beam into a signal light beam and a reference light beam,
  ii) means for irradiating the signal light beam to a measuring site,
  iii) means for shifting a frequency of the reference light beam to a frequency having a slight frequency difference from the frequency of signal beam,
  iv) means for causing a reflected light beam of the signal light beam, which has been reflected from a predetermined deep portion of the measuring site, and the shifted reference light beam to interfere with each other, a heterodyne interference light beam being thereby obtained,
  v) means for dividing the heterodyne interference light beam into first and second divided interference light beams and measuring an intensity of the first and second divided interference light beams, and
  vi) means for acquiring an optical tomography image of the measuring site in accordance with the measured intensity of the first and second divided interference light beams,
  wherein the low coherence light beam is an amplified spontaneous emission light beam, which is radiated out from an optical fiber having been doped with a light emitting material, when excitation energy is applied to the optical fiber,
  wherein the light emitting material is a dye capable of producing fluorescence.

* * * * *